(12) United States Patent
Cady et al.

(10) Patent No.: US 11,083,622 B2
(45) Date of Patent: Aug. 10, 2021

(54) SURGICAL TOOL FOR SEPARATING CAPSULAR BAG FROM LENS IN EYE

(71) Applicants: Kevin J. Cady, Saint Charles, IL (US); Jonathan R. Soiseth, Pomona, CA (US)

(72) Inventors: Kevin J. Cady, Saint Charles, IL (US); Jonathan R. Soiseth, Pomona, CA (US)

(73) Assignee: OnPoint Vision, Inc., Aliso Viejo, CA (US)

( * ) Notice: Subject to any disclaimer, the term of this patent is extended or adjusted under 35 U.S.C. 154(b) by 257 days.

(21) Appl. No.: 16/280,235

(22) Filed: Feb. 20, 2019

(65) Prior Publication Data
US 2019/0269555 A1  Sep. 5, 2019

Related U.S. Application Data

(60) Provisional application No. 62/637,966, filed on Mar. 2, 2018.

(51) Int. Cl.
*A61F 9/007* (2006.01)
*A61F 2/16* (2006.01)
*A61B 90/00* (2016.01)

(52) U.S. Cl.
CPC ........ *A61F 9/00736* (2013.01); *A61F 2/1662* (2013.01); *A61B 2090/0817* (2016.02)

(58) Field of Classification Search
CPC ........ A61B 2090/0817; A61B 17/3211; A61B 17/32053; A61B 17/3213; A61B 2017/32113; A61F 2/1662; A61F 9/007; A61F 9/00736; A61F 9/0133; A61F 9/0136; A61F 9/013; A61F 9/00754
See application file for complete search history.

(56) References Cited

U.S. PATENT DOCUMENTS

| 1,272,170 | A | 7/1918 | Ziegler |
| 5,797,937 | A | 8/1998 | Ichikawa et al. |
| D612,049 | S | 3/2010 | Baynham |
| D785,796 | S | 5/2017 | Efinger et al. |

(Continued)

OTHER PUBLICATIONS

"Steinert DSEK 50 Degree Stripping Spatula", Katena Eye Instruments, available prior to Mar. 2, 2018, 7 pages.

(Continued)

*Primary Examiner* — Majid Jamialahmadi

(57) ABSTRACT

An apparatus includes a handle and a spatula-shaped end coupled to the handle and configured to be inserted into an eye. The spatula-shaped end includes top and bottom surfaces and multiple facets positioned along one or more sides of the spatula-shaped end and along a front of the spatula-shaped end. Each facet narrows a distance between the top and bottom surfaces. One or more first facets are positioned along the front of the spatula-shaped end. The one or more first facets are configured to facilitate insertion of a tip of the spatula-shaped end between an anterior leaflet and a lens in the eye. One or more second facets are positioned along the one or more sides of the spatula-shaped end. The one or more second facets are configured to facilitate sliding of the spatula-shaped end along the anterior leaflet between the anterior leaflet and the lens in the eye.

20 Claims, 6 Drawing Sheets

(56) References Cited

U.S. PATENT DOCUMENTS

| | | | |
|---|---|---|---|
| D898,914 S | 10/2020 | Niver et al. | |
| 2002/0026205 A1* | 2/2002 | Matsutani | A61F 9/0133 606/167 |
| 2004/0010278 A1 | 1/2004 | Nakamura et al. | |
| 2004/0089159 A1 | 5/2004 | Matsutani et al. | |
| 2006/0058824 A1 | 3/2006 | Kozlowski | |
| 2006/0149194 A1 | 7/2006 | Conston et al. | |
| 2010/0023041 A1 | 1/2010 | Satake et al. | |
| 2012/0191114 A1 | 7/2012 | Packard et al. | |
| 2013/0205584 A1 | 8/2013 | Pham et al. | |

OTHER PUBLICATIONS

"Spatula DK", Millennium Surgical, available prior to Mar. 2, 2018, 2 pages.
"Koch Phacoemulsification Spatula", Accutome by Keeler, available prior to Mar. 2, 2018, 2 pages.
"Refractive Instruments", Medizinprodukte—Optha & Technologie, available prior to Mar. 2, 2018, 3 pages.
Katena Eye Instruments Catalog, 2007, 242 pages.
Superior Instruments, "Sheehan Surgical Straight Osteotome 12mm Hexagon Handle", Nov. 2016, 5 pages.
OpenPR, "Ophthalmic Knives Market Competitive Analysis 2019", Sidapharm Greece, Jul. 2019, 4 pages.
Mani, Inc., "Ophthalmic Knife", Dec. 2016, 12 pages.
Qswtitan, "1 pcs Titanium Alloy corneal Epithelium spatula ophthalmic surgical instrument", Apr. 2021, 4 pages.
Notice of Allowance dated Jun. 11, 2021 in connection with U.S. Appl. No. 29/705,169, 10 pages.

\* cited by examiner

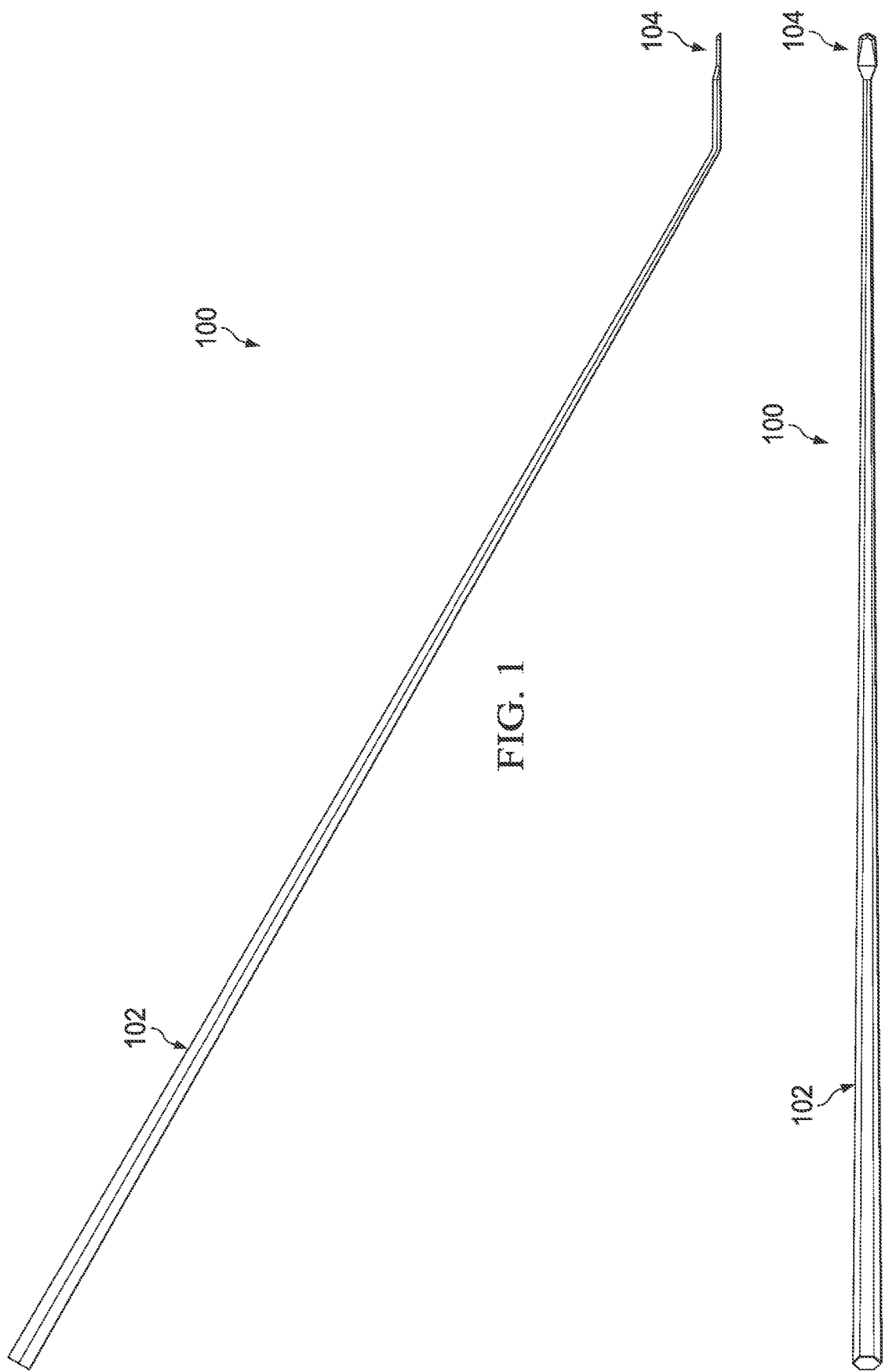

SURGICAL TOOL FOR SEPARATING CAPSULAR BAG FROM LENS IN EYE

CROSS-REFERENCE TO RELATED APPLICATION AND PRIORITY CLAIM

This disclosure claims priority under 35 U.S.C. § 119(e) to U.S. Provisional Patent Application No. 62/637,966 filed on Mar. 2, 2018. This provisional application is hereby incorporated by reference in its entirety.

TECHNICAL FIELD

This disclosure is generally directed to surgical tools. More specifically, this disclosure is directed to a surgical tool for separating a capsular bag from a lens in an eye.

BACKGROUND

Various surgical procedures may be performed on a patient's eye to reduce or correct any number of vision problems. For example, during a capsulotomy, an opening (referred to as a capsulorhexis) is formed in the capsular bag of a patient's eye, allowing the natural crystalline lens of the patient's eye to be removed and replaced with an artificial intraocular lens (IOL). The outer portion of the front side of the capsular bag that remains after the opening is formed in the capsular bag is referred to as the anterior leaflet of the capsular bag. After such a procedure, the anterior leaflet of the capsular bag typically shrinks and undergoes fibrosis during the healing process.

SUMMARY

This disclosure provides a surgical tool for separating a capsular bag from a lens in an eye.

In a first embodiment, an apparatus includes a handle and a spatula-shaped end coupled to the handle and configured to be inserted into an eye. The spatula-shaped end includes top and bottom surfaces and one or more facets positioned along a front of the spatula-shaped end. Each facet narrows a distance between the top and bottom surfaces. The one or more facets are configured to facilitate insertion of a tip of the spatula-shaped end between an anterior leaflet and a lens in the eye.

In a second embodiment, an apparatus includes a handle and a spatula-shaped end coupled to the handle and configured to be inserted into an eye. The spatula-shaped end includes top and bottom surfaces and multiple facets positioned along one or more sides of the spatula-shaped end and along a front of the spatula-shaped end. Each facet narrows a distance between the top and bottom surfaces. The facets include one or more first facets positioned along the front of the spatula-shaped end. The one or more first facets are configured to facilitate insertion of a tip of the spatula-shaped end between an anterior leaflet and a lens in the eye. The facets also include one or more second facets positioned along the one or more sides of the spatula-shaped end. The one or more second facets are configured to facilitate sliding of the spatula-shaped end along the anterior leaflet between the anterior leaflet and the lens in the eye.

In a third embodiment, an apparatus includes a handle having a diameter that tapers along a length of the handle, a spatula-shaped end configured to be inserted into an eye, and a connector coupling the handle and the spatula-shaped end. The connector extends lengthwise from the handle to the spatula-shaped end, and the spatula-shaped end has a maximum width larger than a width of the connector. The spatula-shaped end includes top and bottom surfaces and first and second side surfaces extending between the top and bottom surfaces. The first and second side surfaces are angled towards each other as the first and second side surfaces extend towards a tip of the spatula-shaped end. The spatula-shaped end also includes multiple facets positioned along the first and second side surfaces of the spatula-shaped end and along a front of the spatula-shaped end. Each facet narrows a distance between the top and bottom surfaces. The facets include a first facet positioned at the tip of the spatula-shaped end, a second facet positioned at a location where the first side surface of the spatula-shaped end meets the front of the spatula-shaped end, and a third facet positioned at a location where the second side surface of the spatula-shaped end meets the front of the spatula-shaped end. The facets also include a fourth facet positioned between the first and second facets and a fifth facet positioned between the first and third facets. The facets further include a sixth facet positioned and extending along the first side surface of the spatula-shaped end and a seventh facet positioned and extending along the second side surface of the spatula-shaped end. The first, second, third, fourth, and fifth facets are configured to facilitate insertion of the tip of the spatula-shaped end between an anterior leaflet and a lens in the eye. The sixth and seventh facets are configured to facilitate sliding of the spatula-shaped end along the anterior leaflet between the anterior leaflet and the lens in the eye.

Other technical features may be readily apparent to one skilled in the art from the following figures, descriptions, and claims.

BRIEF DESCRIPTION OF THE DRAWINGS

For a more complete understanding of this disclosure, reference is now made to the following description, taken in conjunction with the accompanying drawing, in which:

FIGS. 1 through 4 illustrate an example surgical tool for separating a capsular bag from a lens in an eye in accordance with this disclosure;

DETAILED DESCRIPTION

Figure 4:
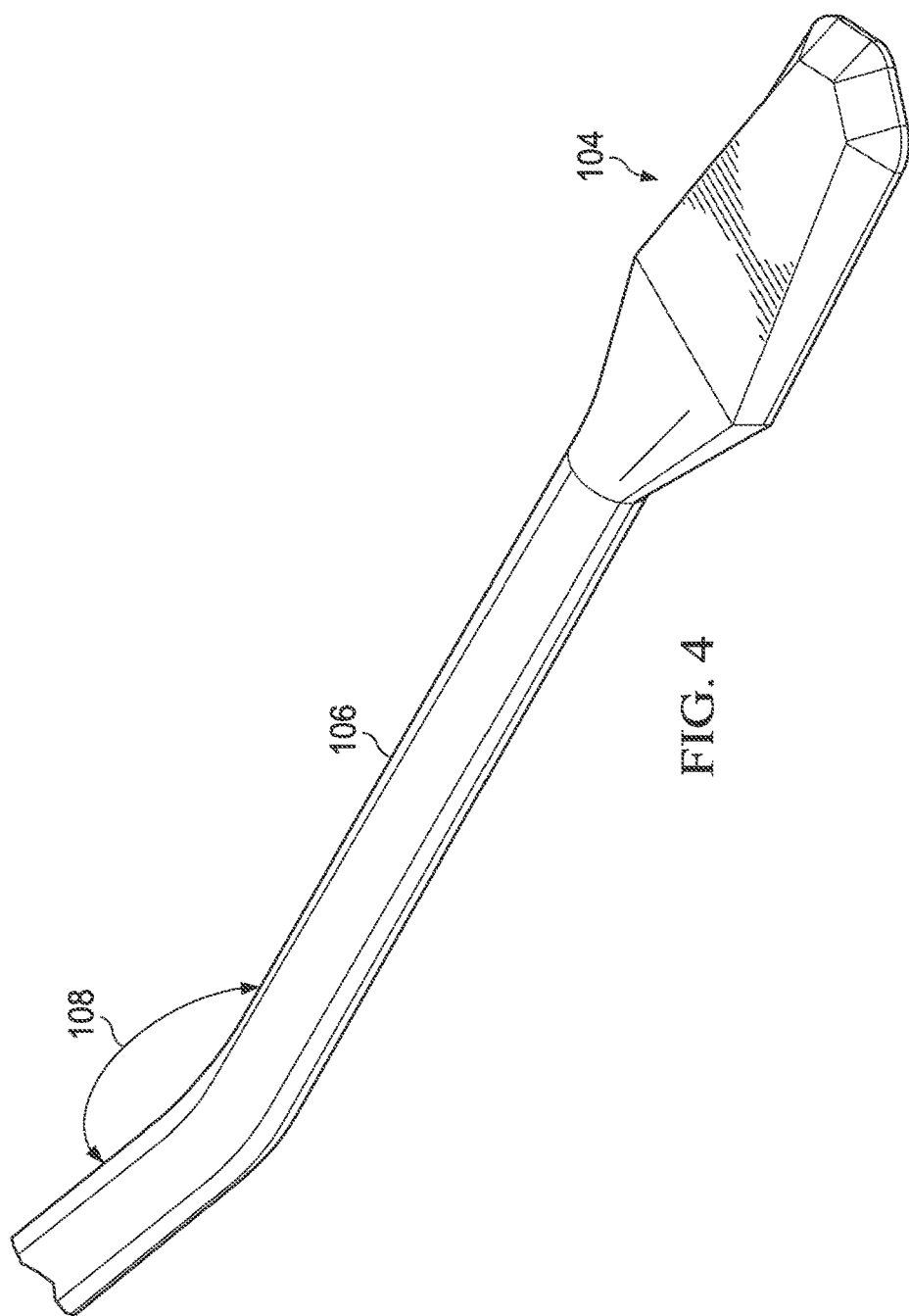

FIGS. 1 through 9, described below, and the various embodiments used to describe the principles of the present invention in this patent document are by way of illustration only and should not be construed in any way to limit the scope of the invention. Those skilled in the art will understand that the principles of the present invention may be implemented in any type of suitably arranged device or system.

As noted above, various surgical procedures may be performed on a patient's eye to reduce or correct any number of vision problems. For example, during a capsulotomy, an opening is formed in the capsular bag of a patient's eye, allowing the natural crystalline lens of the patient's eye to be removed and replaced with an artificial intraocular lens (IOL). This is a common procedure when treating ocular conditions such as cataracts. After such a procedure, the anterior leaflet of the capsular bag typically shrinks and undergoes fibrosis during the healing process, creating a fibrotic ring.

Fibrosis can cause an anterior leaflet of a capsular bag to physically attach itself to an intraocular lens or other lens in a patient's eye. The physical attachment of an anterior leaflet to an intraocular lens or other lens in a patient's eye can be problematic for various reasons. For example, an intraocular lens may need to be removed from a patient's eye, such as when the intraocular lens fails to provide the desired refractive correction in the patient's eye. However, attachment of a fibrotic ring to an intraocular lens can complicate or even prevent removal of the intraocular lens from a patient's eye.

As another example, it may be necessary or desirable to implant an intraocular pseudophakic contact lens (IOPCL) in front of an intraocular lens in a patient's eye, such as to correct a residual refractive error that remains in the patient's eye after implantation of the intraocular lens. The intraocular pseudophakic contact lens may include haptics or other structures that need to extend under the anterior leaflet of the patient's capsular bag in order to secure the intraocular pseudophakic contact lens in place. Attachment of a fibrotic ring to the intraocular lens may complicate or prevent insertion of the haptics of the intraocular pseudophakic contact lens under the anterior leaflet of the patient's capsular bag.

As yet another example, it may be necessary or desirable to remove or replace an existing intraocular pseudophakic contact lens already implanted in a patient's eye, such as to insert a new or more effective intraocular pseudophakic contact lens. Attachment of a fibrotic ring to the existing intraocular pseudophakic contact lens may complicate or prevent removal of the existing intraocular pseudophakic contact lens from the patient's eye.

This disclosure describes a surgical tool that can be used to separate a fibrotic ring or other portion of a capsular bag from an intraocular lens, intraocular pseudophakic contact lens, or other lens in a patient's eye. The surgical tool includes a spatula-shaped end that can be easily positioned between an anterior leaflet and a lens in the patient's eye. In some cases, the surgical tool can be manipulated so that the spatula-shaped end travels along the anterior leaflet, completely separating the anterior leaflet of the patient's capsular bag from the lens. In other cases, the spatula-shaped end can be used to separate the anterior leaflet of the patient's capsular bag from the lens in only certain areas. For instance, the spatula-shaped end can be used to separate the anterior leaflet of the patient's capsular bag from an intraocular lens in specific areas where haptics from an intraocular pseudophakic contact lens are to be inserted between the anterior leaflet and the intraocular lens.

In this way, the surgical tool can be used to partially or completely separate the anterior leaflet of the patient's capsular bag from the lens in the patient's eye. Among other things, this can facilitate easier removal of the lens from the patient's eye or easier coupling of an intraocular pseudophakic contact lens to the lens in the patient's eye.

FIGS. 1 through 4 illustrate an example surgical tool 100 for separating a capsular bag from a lens in an eye in accordance with this disclosure. As shown in FIGS. 1 through 4, the surgical tool 100 includes a handle 102 and a spatula-shaped end 104. The handle 102 represents an elongated structure configured to be held by a surgeon or other personnel and used to manipulate the spatula-shaped end 104. The handle 102 could have any suitable size, shape, and dimensions. In some embodiments, the handle 102 could have a hexagonal or other cross-sectional shape that facilitates easy grasping or manipulation of the handle 102, although any other suitable cross-sectional shape or shapes for the handle 102 could be used.

Figure 3:
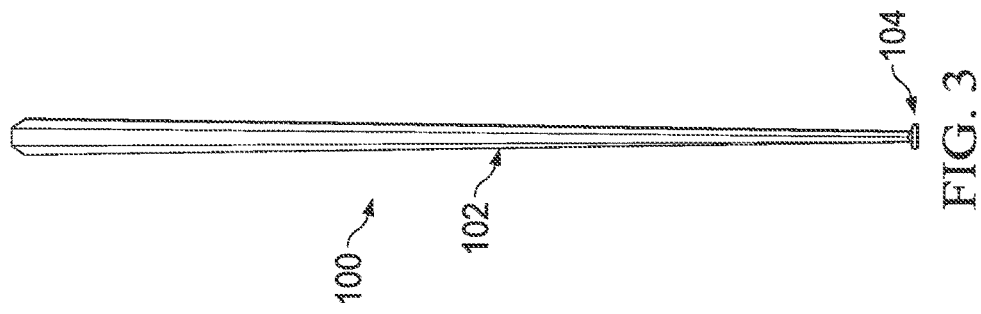

In this example, the handle 102 tapers from a larger cross-sectional size at a free end of the handle 102 (the top end in FIGS. 1 and 3) to a smaller cross-sectional size at the opposing end of the handle 102 (the bottom end in FIGS. 1 and 3). The larger cross-sectional size allows the handle 102 to be held and manipulated more easily, while the smaller cross-sectional size allows the handle 102 to be used near or in a patient's eye. Note that while the tapering of the handle 102 is generally constant along the length of the handle 102 here, this need not be the case. For instance, the handle 102 could have a larger constant cross-sectional size along most of the handle 102 where the tool 100 may be held, and the handle 102 could have an immediate or sharp transition to a smaller cross-sectional size in the area where the handle 102 would be near or enter into a patient's eye. Of course, other configurations of the handle 102 could also be used, including those configurations in which the handle 102 does not taper in cross-sectional size.

The spatula-shaped end 104 of the surgical tool 100 is sized and shaped to be inserted under the capsular bag in a patient's eye (such as under a fibrotic ring of the capsular bag) in order to at least partially separate the capsular bag from a lens in the patient's eye. As noted above, the tool 100 can be manipulated so that the spatula-shaped end 104 travels along the anterior leaflet, completely separating the patient's capsular bag from the lens. Alternatively, the spatula-shaped end 104 can be used to separate the anterior leaflet of the patient's capsular bag from the lens in only certain areas. The phrase "spatula-shaped" refers to a shape in which two opposing major surfaces define a generally flat and thin structure.

As shown in FIG. 4, a connecting portion 106 of the surgical tool 100 joins the spatula-shaped end 104 to the handle 102. Part of the connecting portion 106 can be inserted into a patient's eye in order to allow the spatula-shaped end 104 to be moved within the patient's eye. The connecting portion 106 has a small cross-sectional size so that the surgical tool 100 can be easily rotated or otherwise moved while the spatula-shaped end 104 is inserted in the patient's eye. In some embodiments, the connecting portion 106 has a circular cross-sectional shape, although other cross-sectional shapes could be used. Also, in this example, the connecting portion 106 is generally linear (straight) between the handle 102 and the spatula-shaped end 104, meaning the connecting portion 106 extends lengthwise between the handle 102 and the spatula-shaped end 104. However, this need not be the case. In addition, the connecting portion 106 may have a generally-constant cross-sectional size along its length, or the cross-sectional size of the connecting portion 106 may vary. Note that the connecting portion 106 could represent part of the handle 102, part of the spatula-shaped end 104, or a separate and distinct part of the surgical tool 100.

The spatula-shaped end 104 here is angled with respect to the handle 102, meaning the spatula-shaped end 104 is not linearly aligned with respect to the handle 102. An angle 108 between the handle 102 and the spatula-shaped end 104/connecting portion 106 could have any suitable value. In some embodiments, an angle 108 of about 150° is formed between the handle 102 and the spatula-shaped end 104/connecting portion 106. Of course, other suitable angles could be used, and the angle could be adjustable (such as based on physical modification to the connecting portion 106 of the surgical tool 100).

The surgical tool 100 could be formed from any suitable biocompatible material(s), such as steel or other metal(s) or material(s) that can be adequately sterilized. The surgical tool 100 could also be formed in any suitable manner, such as machining, injection molding, or casting followed by polishing. The surgical tool 100 could be formed as an integral device or as separate components that are connected together. Depending on the implementation, the surgical tool 100 could be used with multiple patients (with cleaning and sterilization in between uses) or provided sterile and used with a single patient or a single eye and then discarded.

Particular embodiments of the surgical tool 100 may have one, some, or all of the following characteristics. The handle 102 could have an overall length of about 100 millimeters. The handle 102 could have a maximum diameter of about 2 millimeters at the top of the handle 102 and taper to a narrower diameter of about 0.5 millimeters at the bottom of the handle 102. The connecting portion 106 could have a diameter of about 0.5 millimeters. A combined length of the spatula-shaped end 104 and the connecting portion 106 could be about 8.23 millimeters.

Although FIGS. 1 through 4 illustrate one example of a surgical tool 100 for separating a capsular bag from a lens in an eye, various changes may be made to FIGS. 1 through 4. For example, the shapes and relative sizes of the components of the tool 100 could vary as needed or desired. Also, the dimensions, angles, and other specific numerical values provided above relate to specific implementations of the surgical tool 100. Other implementations of the surgical tool 100 could have any other suitable dimensions, angles, and other specific numerical values.

Figure 5:
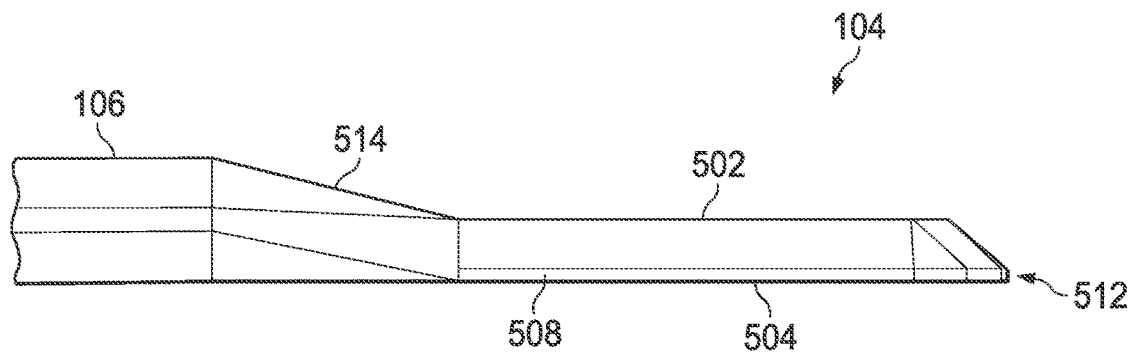
FIGS. 5 through 7 illustrate an example spatula-shaped end of a surgical tool for separating a capsular bag from a lens in an eye in accordance with this disclosure.
Figure 6:
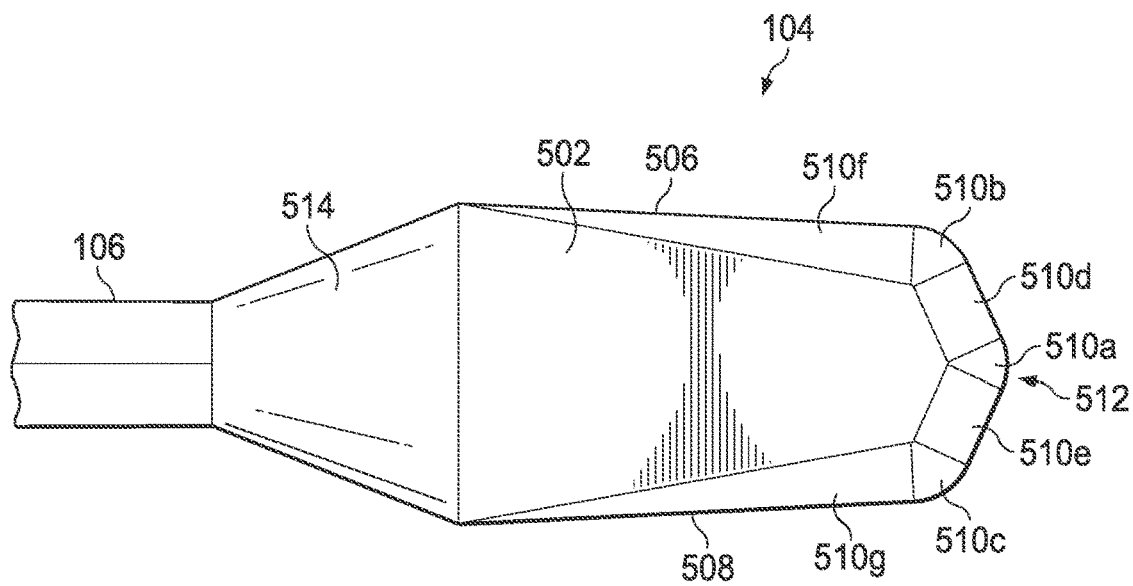
Figure 7:
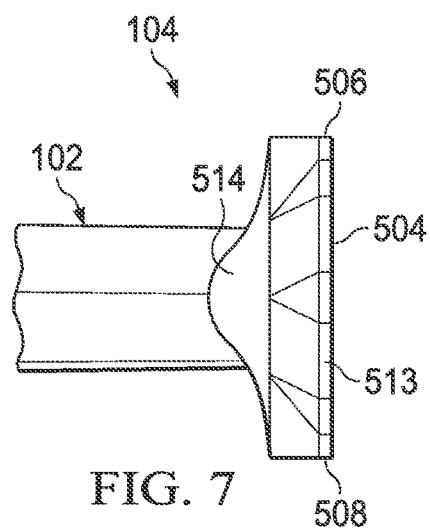

FIGS. 5 through 7 illustrate an example spatula-shaped end 104 of a surgical tool 100 for separating a capsular bag from a lens in an eye in accordance with this disclosure. In particular, FIG. 5 illustrates an example side view of the spatula-shaped end 104, FIG. 6 illustrates an example top view of the spatula-shaped end 104, and FIG. 7 illustrates an example front view of the spatula-shaped end 104. For ease of explanation, the spatula-shaped end 104 shown in FIGS. 5 through 7 is described as forming part of the surgical tool 100 shown in FIGS. 1 through 4. However, the spatula-shaped end 104 shown in FIGS. 5 through 7 could form part of any other surgical tool, such as a surgical tool having a different handle.

As shown in FIGS. 5 through 7, the spatula-shaped end 104 includes a major top surface 502, a major bottom surface 504, side surfaces 506 and 508, and various facets 510a-510g. The top and bottom surfaces 502 and 504 in this example represent generally flat surfaces, although each surface 502 and 504 could have any other suitable shape (such as a surface with a slight convexity or concavity). In some embodiments, the top and bottom surfaces 502 and 504 can be substantially parallel to one another, although a slight angling of the top and bottom surfaces 502 and 504 could also be permitted. The thickness of the spatula-shaped end 104 as measured between the top and bottom surfaces 502 and 504 can be small in order to permit insertion of the spatula-shaped end 104 between the anterior leaflet and the lens of a patient's eye.

The side surfaces 506 and 508 of the spatula-shaped end 104 in this example represent generally straight sides that angle slightly towards one another. However, the side surfaces 506 and 508 need not be straight and could have curved or other shapes. Also, the side surfaces 506 and 508 need not angle towards one another and could be parallel or angle away from each other. In some embodiments, the side surfaces 506 and 508 of the spatula-shaped end 104 can extend between the top and bottom surfaces 502 and 504.

The facets 510a-510g represent angled or curved surfaces that narrow the distance between the top and bottom surfaces 502 and 504 of the spatula-shaped end 104, thereby narrowing the thickness of the spatula-shaped end 104. In this example, there are five facets 510a-510e positioned along the front of the spatula-shaped end 104, and there are two additional elongated facets 510f-510g extending along the sides of the spatula-shaped end 104. In particular, the facet 510a is located at a tip 512 of the spatula-shaped end 104. The facet 510b is located where one side of the spatula-shaped end 104 meets the front of the spatula-shaped end 104, and the facet 510c is located where another side of the spatula-shaped end 104 meets the front of the spatula-shaped end 104. The facet 510d is positioned between the facets 510a and 510b, and the facet 510e is positioned between the facets 510a and 510c. The facet 510f extends along part or all of one side of the spatula-shaped end 104 and meets the facet 510b, and the facet 510g extends along part or all of the other side of the spatula-shaped end 104 and meets the facet 510c. The "front" of the spatula-shaped end 104 refers to the free end of the spatula-shaped end 104 opposite the handle 102/connecting portion 106.

In this particular example, the facets 510a, 510b, and 510c appear generally as smaller triangles, the facets 510d and 510e appear generally as rectangles, and the facets 510e and 510f appear generally as elongated larger triangles when viewed from above. However, this is for illustration only, and each of the various facets 510a-510g can generally have any suitable size and shape.

The facets 510a-510e positioned along the front of the spatula-shaped end 104 allow for easier insertion of the spatula-shaped end 104 between the anterior leaflet and the lens of a patient's eye. For example, as can be seen in FIG. 5, the facets 510a-510e narrow the thickness of the spatula-shaped end 104 approaching the tip 512 of the spatula-shaped end 104, which makes it easier to insert the spatula-shaped end 104 between the anterior leaflet and the lens in a patient's eye. In some embodiments, the thickness of the spatula-shaped end 104 narrows so that a small surface 513 extends between the top and bottom surfaces 502 and 504 of the spatula-shaped end 104. The surface 513 here could have a flat, convex, or other shape. In other embodiments, the flat surface 513 can be omitted, and the facets 510a-510e can extend all the way to the bottom surface 504. The facets 510f-510g extending along the sides of the spatula-shaped end 104 allow for easier movement of the spatula-shaped end 104 side-to-side, such as when a surgeon is sliding the spatula-shaped end 104 along a fibrotic ring of the anterior leaflet. Note, however, that other numbers or arrangements of facets could be used in the tool 100 to support insertion and movement of the spatula-shaped end 104. The facets 510a-510g could represent straight surfaces or curved surfaces (such as surfaces with slight concavities).

Note that it is possible to omit one or more of the facets 510a-510g from the spatula-shaped end 104. For example, one or both of the facets 510f-510g could be omitted from the spatula-shaped end 104. As another example, at least some of the facets 510a-510e could be combined.

In this example, the front of the spatula-shaped end 104 has a rounded tip 512, which again can allow for easier insertion of the spatula-shaped end 104 between the anterior leaflet and the lens of a patient's eye. However, the tip 512 could also be pointed or have any other suitable shape. Also, in this example, flat surfaces form the side surfaces 506 and 508 and extend around the front of the spatula-shaped end 104 to meet at the tip 512. However, the side surfaces 506 and 508 could have any other suitable form, and the front of the spatula-shaped end 104 need not include the small surface 513 running along the edge with the bottom surface 504.

A transition area 514 represents a portion of the spatula-shaped end 104 that joins with the connecting portion 106 of the surgical tool 100. As shown in FIG. 6, the width of the transition area 514 tapers from a smaller width (where the transition area 514 joins the connecting portion 106) to a larger width (where the transition area 514 joins the remainder of the spatula-shaped end 104). The width of the transition area 514 therefore decreases as the transition area 514 approaches the connecting portion 106. As shown in FIG. 5, the thickness of the transition area 514 tapers from a larger thickness (where the transition area 514 joins the connecting portion 106) to a smaller thickness (where the transition area 514 joins the remainder of the spatula-shaped end 104). The thickness of the transition area 514 therefore increases as the transition area 514 approaches the connecting portion 106. Thus, the transition area 514 has a maximum thickness that is larger than the thickness of other portions of the spatula-shaped end 104 and could taper or transition between the larger diameter of the connecting portion 106 and the smaller thickness of the spatula-shaped end 104.

In this example, the transition area 514 has a flat bottom surface that is planar with the bottom surface 504 and an angled or curved top surface that angles away from the top surface 502. However, the transition area 514 need not have a planar bottom surface and could instead have a bottom surface with a convex, concave, or other shape. Also, the transition area 514 need not have an angled or curved top surface and could instead have a top surface with a stepped, straight, or other shape. In general, the transition area 514 could have any other suitable form.

During use, an incision can be formed in a patient's eye, and the spatula-shaped end 104 and part or all of the connecting portion 106 of the surgical tool 100 can be inserted into the patient's eye. The tool 100 can be manipulated so that the tip 512 of the spatula-shaped end 104 is pushed between an anterior leaflet of a capsular bag and a lens in the patient's eye. The spatula-shaped end 104 can be positioned between the anterior leaflet and the lens so that part or all of the top surface 502 is contacting the anterior leaflet and part or all of the bottom surface 504 is contacting the lens. This separates a portion of the anterior leaflet from the lens. If desired, the spatula-shaped end 104 can be manipulated to slide along the anterior leaflet and separate all of the anterior leaflet from the lens. Alternatively, the spatula-shaped end 104 can be removed and reinserted in another area (possibly through a different incision in the patient's eye) to separate another portion of the anterior leaflet from the lens. Of course, other uses for the surgical tool 100 are also possible.

Particular embodiments of the spatula-shaped end 104 may have one, some, or all of the following characteristics. An overall length of the spatula-shaped end 104 could be about 3.25 millimeters. The transition area 514 could extend about 1.0 millimeters of that length, the straight side surfaces 506 and 508 of the spatula-shaped end 104 could extend about 2.0 millimeters of that length, and the front facets 510a-510e could extend about 0.25 millimeters of that length. A maximum width of the spatula-shaped end 104 could be about 1.3 millimeters, and the straight sides of the spatula-shaped end 104 could taper from that width to a width of about 1.1 millimeters. The transition area 514 could taper from the maximum width of the spatula-shaped end 104 (about 1.3 millimeters) to the diameter of the connecting portion 106 (about 0.5 millimeters). The facets 510a-510c could each have a radius of curvature of about 0.25 millimeters. The maximum thickness of the spatula-shaped end 104 between the flat top and bottom surfaces 502 and 504 could be about 0.25 millimeters, and the surface 513 could have a height of about 0.05 millimeters.

Although FIGS. 5 through 7 illustrate one example of a spatula-shaped end 104 of a surgical tool 100 for separating a capsular bag from a lens in an eye, various changes may be made to FIGS. 5 through 7. For example, the shapes and relative sizes of the components of the spatula-shaped end 104 could vary as needed or desired. Also, the dimensions and other specific numerical values provided above relate to specific implementations of the spatula-shaped end 104, and other implementations of the spatula-shaped end 104 could have any other suitable dimensions and other specific numerical values.

Figure 8A:
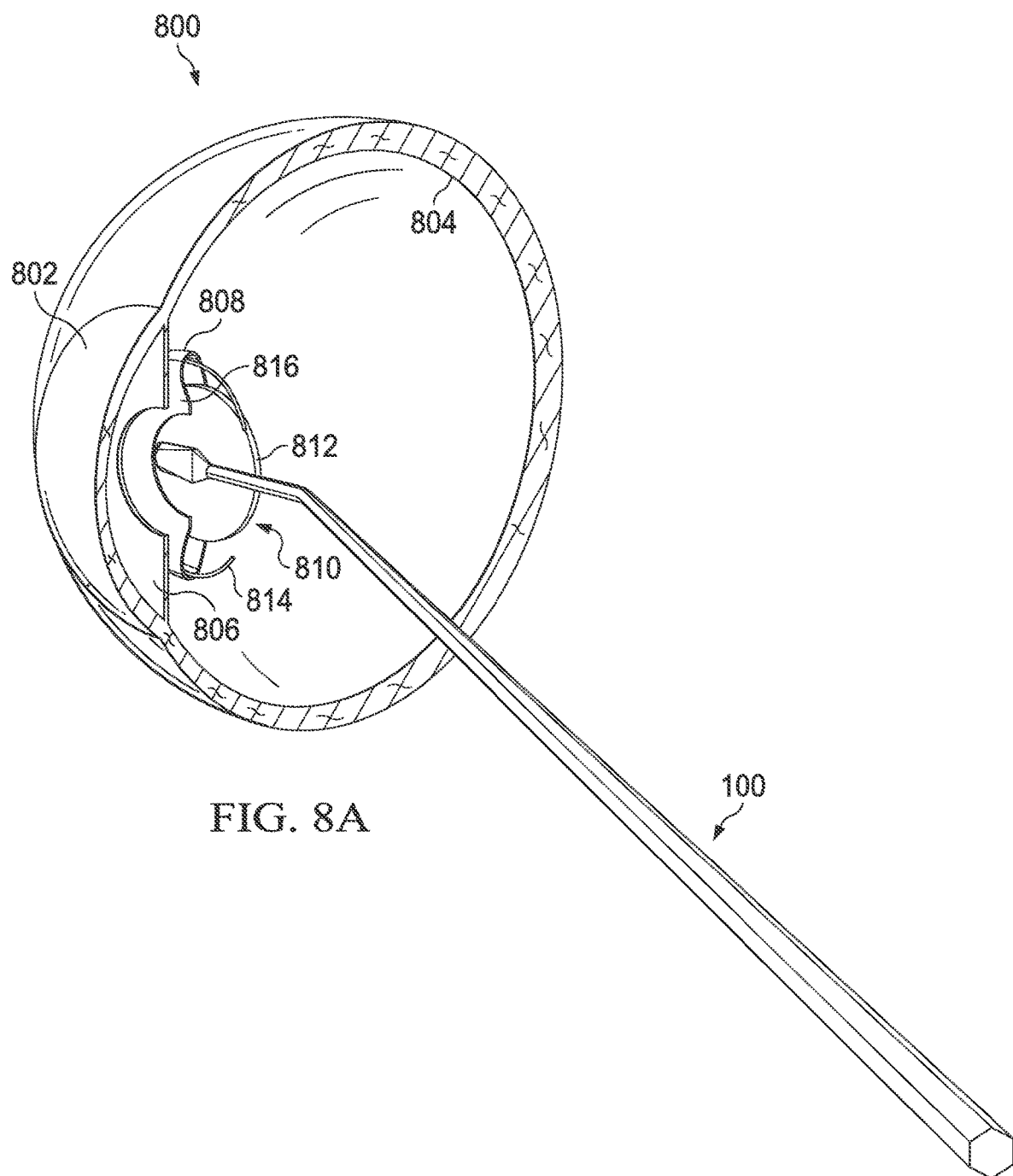
FIGS. 8A and 8B illustrate a first example use of a surgical tool for separating a capsular bag from a lens in an eye in accordance with this disclosure.
Figure 8B:
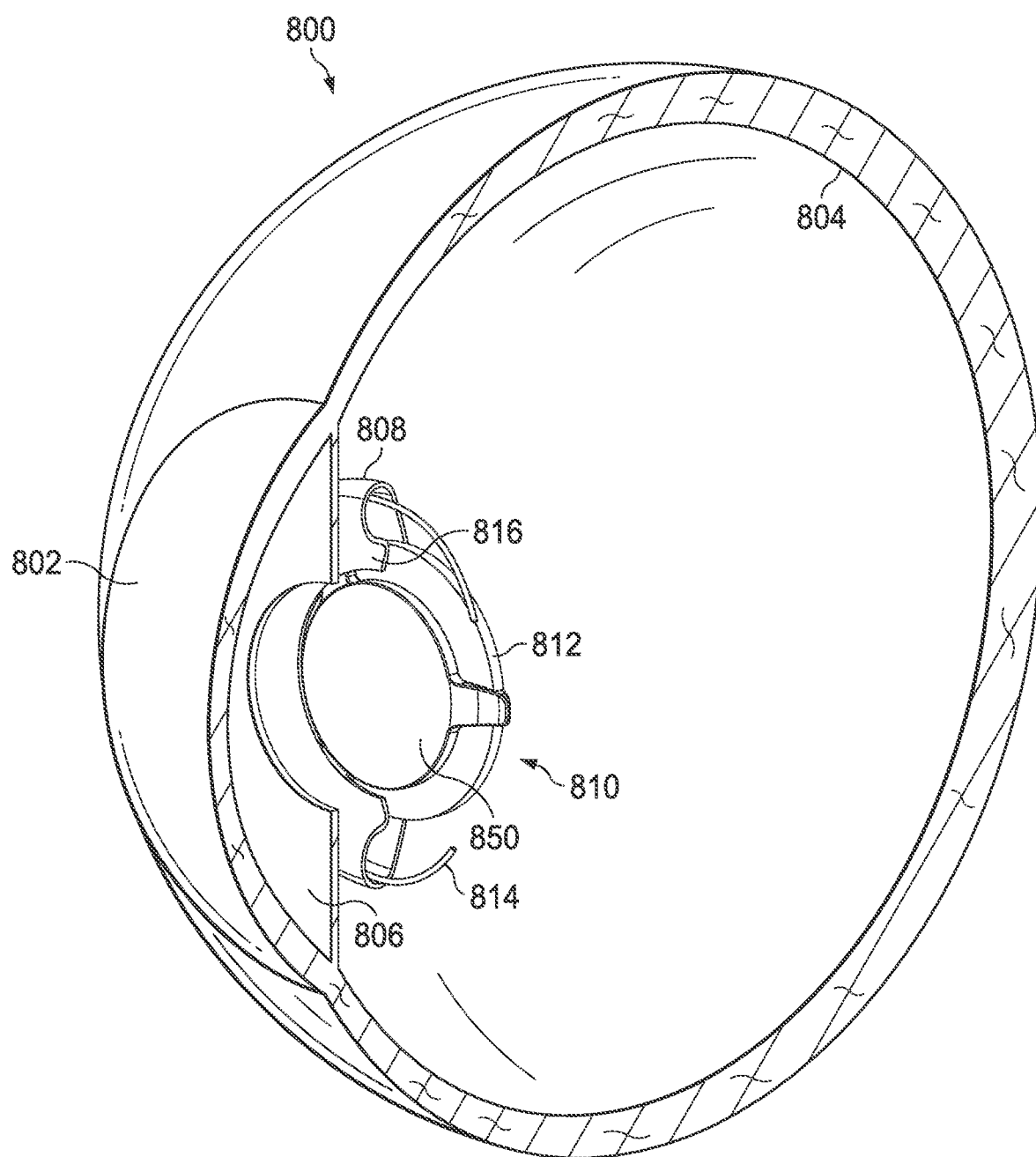

FIGS. 8A and 8B illustrate example uses of a surgical tool for separating a capsular bag from a lens in an eye 800 in accordance with this disclosure. As shown in FIG. 8A, the eye 800 includes a cornea 802, a sclera 804, and an iris 806. The cornea 802 represents the clear front portion of the eye 800 through which light passes to enter into the eye 800. The sclera 804 is the tough outer white portion of the eye. The iris 806 controls the size of the eye's pupil to thereby control the amount of light from the cornea 802 that enters into the interior of the eye 800.

The eye 800 also includes a capsular bag 808, which typically holds the natural crystalline lens of the eye 800. However, in this example, the natural crystalline lens has been removed and replaced with an intraocular lens 810 having an optical lens 812 and one or more haptics 814. The optical lens 812 of the intraocular lens 810 receives light entering the eye and focuses the light onto the retina of the eye 800. The haptics 814 of the intraocular lens 810 help to hold the intraocular lens 810 within the capsular bag 808 so that the optical lens 812 of the intraocular lens 810 is in a desired position within the eye 800.

In this example, the surgical tool 100 described above can be used to help separate a fibrotic ring or other portion of the anterior leaflet 816 at least partially from the intraocular lens 810. For example, the spatula-shaped end 104 of the surgical tool 100 can be inserted between the anterior leaflet 816 and the intraocular lens 810, and the spatula-shaped end 104 can be moved along the anterior leaflet 816 to completely separate the anterior leaflet 816 from the intraocular lens 810. At this point, the intraocular lens 810 could be removed.

As shown in FIG. 8B, an intraocular pseudophakic contact lens 850 can optionally be placed on the intraocular lens 810 within the capsular bag 808. The intraocular pseudophakic contact lens 850 alters the light reaching the intraocular lens 810, which may allow the intraocular pseudophakic contact lens 850 to correct any residual refractive errors that remain in the eye 800 after implantation of the intraocular lens 810. Details of example intraocular pseudophakic contact lenses that could be used here can be found in U.S. patent application Ser. No. 14/860,629 filed on Sep. 21, 2015 and U.S. patent application Ser. No. 15/646,254 filed on Jul. 11, 2017 (both of which are hereby incorporated by reference in their entirety). The intraocular pseudophakic contact lens 850 here is placed on the anterior surface of the intraocular lens 810, meaning the front surface of the intraocular lens 810 with respect to the eye 800. Light enters through the cornea 802 and passes through the pupil before entering the intraocular pseudophakic contact lens 850, which modifies the light. The modified light then passes through the optical lens 812 of the intraocular lens 810 and is again modified. The twice-modified light then travels through the remainder of the eye 800 to reach the retina at the back of the eye 800.

The intraocular pseudophakic contact lens 850 can include one or more haptics that extend a short distance and fit under an anterior leaflet 816 of the capsular bag 808. This allows the haptics to be captured and confined by the anterior leaflet 816 (and possibly attach to the anterior leaflet 816 via fibrosis or re-fibrosis). The anterior leaflet 816 represents the outer portion of the front side of the capsular bag 808 that remains after a capsulorhexis is formed in the capsular bag 808. The insertion of the haptics of the intraocular pseudophakic contact lens 850 under the anterior leaflet 816 helps to secure the intraocular pseudophakic contact lens 850 in place. Note that the haptics of the intraocular pseudophakic contact lens 850 are shorter or smaller than the haptics 814 of the intraocular lens 810. This is because the haptics 814 of the intraocular lens 810 extend generally to the top and bottom of the capsular bag 808 and help to hold the intraocular lens 810 in the proper positon within the capsular bag 808. The haptics of the intraocular pseudophakic contact lens 850 need not extend to the top and bottom of the capsular bag 808 and instead may only extend a short distance under the anterior leaflet 816.

In this example, the surgical tool 100 described above can be used to help separate a fibrotic ring or other portion of the anterior leaflet 816 at least partially from the intraocular lens 810 or from the intraocular pseudophakic contact lens 850. For example, the spatula-shaped end 104 of the surgical tool 100 can be inserted between the anterior leaflet 816 and the intraocular lens 810, and the spatula-shaped end 104 can be moved along the anterior leaflet 816 to completely separate the anterior leaflet 816 from the intraocular lens 810. At this point, the intraocular pseudophakic contact lens 850 could be placed on the intraocular lens 810 with its haptics inserted under the anterior leaflet 816. Alternatively, the spatula-shaped end 104 could be inserted between the anterior leaflet 816 and the intraocular lens 810 in multiple locations to partially separate the anterior leaflet 816 from the intraocular lens 810 at those locations only. At that point, the intraocular pseudophakic contact lens 850 could be placed on the intraocular lens 810 with its haptics inserted under the anterior leaflet 816 at those locations. As yet another example, the spatula-shaped end 104 of the surgical tool 100 can be inserted between the anterior leaflet 816 and the intraocular pseudophakic contact lens 850 in order to separate the anterior leaflet 816 from the intraocular pseudophakic contact lens 850, such as during removal or replacement of the intraocular pseudophakic contact lens 850.

Although FIGS. 8A and 8B illustrate examples of uses of a surgical tool 100 for separating a capsular bag from a lens in an eye, various changes may be made to FIGS. 8A and 8B. For example, the surgical tool 100 could be used in any other suitable manner and need not be used to separate an intraocular lens from a capsular bag. Also, the specific forms of the intraocular lens 810 and the intraocular pseudophakic contact lens 850 shown here are for illustration only. Various designs for intraocular lenses are known in the art, and various intraocular pseudophakic contact lenses are shown and described in U.S. patent application Ser. No. 14/860,629 and U.S. patent application Ser. No. 15/646,254.

Figure 9:
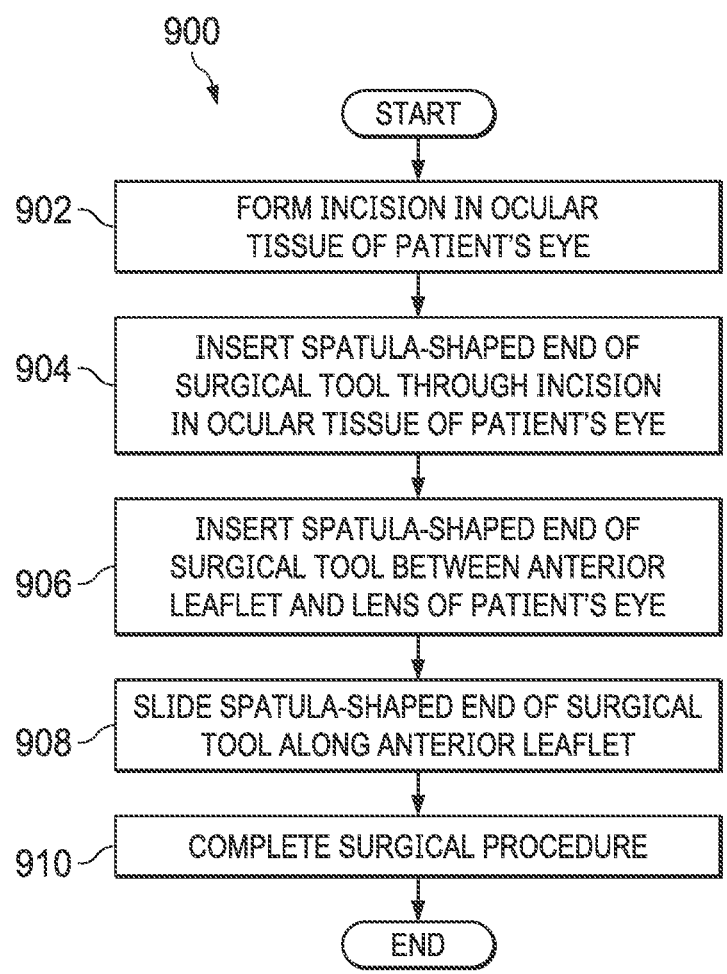
FIG. 9 illustrates an example method for using a surgical tool to separate a capsular bag from a lens in an eye in accordance with this disclosure.

FIG. 9 illustrates an example method 900 for using a surgical tool to separate a capsular bag from a lens in an eye in accordance with this disclosure. For ease of explanation, the method 900 shown in FIG. 9 is described as involving the use of the surgical tool 100 shown in FIGS. 1 through 4 with the spatula-shaped end 104 shown in FIGS. 5 through 7. However, the method 900 could be used with any other suitable surgical tool having any other suitable spatula-shaped end.

As shown in FIG. 9, an incision is formed in ocular tissue of a patient's eye at step 902. This could include, for example, a surgeon forming an incision in the cornea 802 of the patient's eye. The incision can be formed manually with a surgical blade or using a surgical tool that moves a surgical blade. A spatula-shaped end of a surgical tool is inserted through the incision into the patient's eye at step 904. This could include, for example, the surgeon manipulating the handle 102 of the surgical tool 100 and inserting the spatula-shaped end 104 of the surgical tool 100 through the incision. Part or all of the connecting portion 106 of the surgical tool 100 can also be inserted through the incision.

At least part of the spatula-shaped end is inserted between an anterior leaflet and a lens in the patient's eye at step 906. This could include, for example, the surgeon manipulating the handle 102 of the surgical tool 100 and pushing the spatula-shaped end 104 of the surgical tool 100 between the anterior leaflet 816 and a lens in the patient's eye. The lens could represent an intraocular lens 810, an intraocular pseudophakic contact lens 850, or other lens present in the patient's eye.

Optionally, the spatula-shaped end of the surgical tool can slide along the anterior leaflet in the patient's eye at step 908. This could include, for example, the surgeon manipulating the handle 102 of the surgical tool 100 and pushing the spatula-shaped end 104 of the surgical tool 100 sideways along the anterior leaflet 816. As noted above, this can be done to substantially or completely separate the anterior leaflet 816 from the lens in the patient's eye. However, as noted above, this need not occur. For instance, steps 902-906 can be repeated multiple times to separate multiple distinct portions of the anterior leaflet 816 from the lens in the patient's eye, without completely separating the anterior leaflet 816 from the lens in the patient's eye.

A surgical procedure can be completed at step 910. This could include, for example, a surgeon removing the lens (which could be completely separated from the anterior leaflet 816 using the surgical tool 100) from the patient's eye. Alternatively, this could include the surgeon inserting an intraocular pseudophakic contact lens into the patient's eye and securing haptics of the intraocular pseudophakic contact lens under the anterior leaflet 816 in the patient's eye (in areas where the anterior leaflet 816 was separated from the lens using the surgical tool 100). Note, however, that the surgical tool 100 could be used for any other suitable purpose.

Although FIG. 9 illustrates one example of a method 900 for using a surgical tool to separate a capsular bag from a lens in an eye, various changes may be made to FIG. 9. For example, while shown as a series of steps, various steps shown in FIG. 9 could overlap, occur in parallel, or occur multiple times.

It may be advantageous to set forth definitions of certain words and phrases used throughout this patent document. The terms "include" and "comprise," as well as derivatives thereof, mean inclusion without limitation. The term "or" is inclusive, meaning and/or. The phrase "associated with," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, have a relationship to or with, or the like. The phrase "at least one of," when used with a list of items, means that different combinations of one or more of the listed items may be used, and only one item in the list may be needed. For example, "at least one of: A, B, and C" includes any of the following combinations: A, B, C, A and B, A and C, B and C, and A and B and C.

The description in the present application should not be read as implying that any particular element, step, or function is an essential or critical element that must be included in the claim scope. The scope of patented subject matter is defined only by the allowed claims. Moreover, none of the claims invokes 35 U.S.C. § 112(f) with respect to any of the appended claims or claim elements unless the exact words "means for" or "step for" are explicitly used in the particular claim, followed by a participle phrase identifying a function. Use of terms such as (but not limited to) "mechanism," "module," "device," "unit," "component," "element," "member," "apparatus," "machine," "system," "processor," or "controller" within a claim is understood and intended to refer to structures known to those skilled in the relevant art, as further modified or enhanced by the features of the claims themselves, and is not intended to invoke 35 U.S.C. § 112(f).

While this disclosure has described certain embodiments and generally associated methods, alterations and permutations of these embodiments and methods will be apparent to those skilled in the art. Accordingly, the above description of example embodiments does not define or constrain this disclosure. Other changes, substitutions, and alterations are also possible without departing from the spirit and scope of this disclosure, as defined by the following claims.

What is claimed is:

1. An apparatus comprising:
  a handle; and
  a spatula-shaped end coupled to the handle and configured to be inserted into an eye, the spatula-shaped end comprising:
    top and bottom surfaces;
    first and second side surfaces extending between the top and bottom surfaces;
    a first facet positioned at a tip of the spatula-shaped end;
    a second facet positioned at a location where the first side surface meets a front of the spatula-shaped end;
    a third facet positioned at a location where the second side surface meets the front of the spatula-shaped end;
    a fourth facet positioned between the first and second facets;
    a fifth facet positioned between the first and third facets;
    a sixth facet positioned and extending along the first side surface; and
    a seventh facet positioned and extending along the second side surface;
  wherein the first, second, third, fourth, and fifth facets are configured to facilitate insertion of the tip of the spatula-shaped end between an anterior leaflet and a lens in the eye.

2. The apparatus of claim 1, wherein the apparatus forms a non-linear handheld tool.

3. The apparatus of claim 1, wherein:
  each of the top and bottom surfaces is substantially flat; and
  the top and bottom surfaces are substantially parallel.

4. The apparatus of claim 1, wherein the first and second side surfaces are angled towards each other as the first and second side surfaces extend towards the tip of the spatula-shaped end.

5. The apparatus of claim 1, further comprising:
  a connector coupling the handle and the spatula-shaped end, the connector narrower than at least part of the handle.

6. The apparatus of claim 5, wherein a portion of the connector is configured to be inserted into the eye.

7. The apparatus of claim 5, wherein:
  the spatula-shaped end further comprises a transition area coupled to the connector; and
  the transition area has a width that decreases as the transition area approaches the connector.

8. The apparatus of claim 7, wherein the transition area comprises:
  a bottom that is planar with the bottom surface; and
  a top that extends above the top surface.

9. An apparatus comprising:
  a handle; and
  a spatula-shaped end coupled to the handle and configured to be inserted into an eye, the spatula-shaped end comprising:
    top and bottom surfaces;
    first and second side surfaces extending between the top and bottom surfaces; and
    multiple facets each narrowing a distance between the top and bottom surfaces;
  wherein the multiple facets include:
    a first facet positioned at a tip of the spatula-shaped end;
    a second facet positioned at a location where the first side surface meets a front of the spatula-shaped end;
    a third facet positioned at a location where the second side surface meets the front of the spatula-shaped end;
    a fourth facet positioned between the first and second facets;
    a fifth facet positioned between the first and third facets;
    a sixth facet positioned and extending along the first side surface; and
    a seventh facet positioned and extending along the second side surface; and
  wherein the multiple facets are configured to facilitate insertion of the tip of the spatula-shaped end between an anterior leaflet and a lens in the eye and sliding of the spatula-shaped end along the anterior leaflet between the anterior leaflet and the lens in the eye.

10. The apparatus of claim 9, wherein each of the sixth and seventh facets is elongated and extends along a single side of the spatula-shaped end.

11. The apparatus of claim 9, wherein:
  each of the top and bottom surfaces is substantially flat; and
  the top and bottom surfaces are substantially parallel.

12. The apparatus of claim 9, wherein the first and second side surfaces are angled towards each other as the first and second side surfaces extend towards the tip of the spatula-shaped end.

13. The apparatus of claim 9, further comprising:
  a connector coupling the handle and the spatula-shaped end, the connector narrower than at least part of the handle.

14. The apparatus of claim 13, wherein a portion of the connector is configured to be inserted into the eye.

15. The apparatus of claim 13, wherein:
the spatula-shaped end further comprises a transition area coupled to the connector; and
the transition area has a thickness that increases as the transition area approaches the connector.

16. The apparatus of claim 15, wherein the transition area comprises:
a bottom that is planar with the bottom surface; and
a top that extends above the top surface.

17. An apparatus comprising:
a handle having a diameter that tapers along a length of the handle;
a spatula-shaped end configured to be inserted into an eye; and
a connector coupling the handle and the spatula-shaped end, the connector extending lengthwise from the handle to the spatula-shaped end, the spatula-shaped end having a maximum width larger than a width of the connector;
wherein the spatula-shaped end comprises:
top and bottom surfaces;
first and second side surfaces extending between the top and bottom surfaces, the first and second side surfaces angled towards each other as the first and second side surfaces extend towards a tip of the spatula-shaped end; and
multiple facets positioned along the first and second side surfaces of the spatula-shaped end and along a front of the spatula-shaped end, each facet of the multiple facets narrowing a distance between the top and bottom surfaces;
wherein the facets include:
a first facet positioned at the tip of the spatula-shaped end;
a second facet positioned at a location where the first side surface of the spatula-shaped end meets the front of the spatula-shaped end;
a third facet positioned at a location where the second side surface of the spatula-shaped end meets the front of the spatula-shaped end;
a fourth facet positioned between the first and second facets;
a fifth facet positioned between the first and third facets;
a sixth facet positioned and extending along the first side surface of the spatula-shaped end; and
a seventh facet positioned and extending along the second side surface of the spatula-shaped end;
wherein the first, second, third, fourth, and fifth facets are configured to facilitate insertion of the tip of the spatula-shaped end between an anterior leaflet and a lens in the eye; and
wherein the sixth and seventh facets are configured to facilitate sliding of the spatula-shaped end along the anterior leaflet between the anterior leaflet and the lens in the eye.

18. The apparatus of claim 17, wherein:
each of the top and bottom surfaces is substantially flat; and
the top and bottom surfaces are substantially parallel.

19. The apparatus of claim 18, wherein:
the spatula-shaped end further comprises a transition area coupled to the connector;
the transition area has a thickness that increases as the transition area approaches the connector; and
the transition area has a width that decreases as the transition area approaches the connector.

20. The apparatus of claim 17, wherein:
the handle has a hexagonal cross-sectional shape; and
the connector extends linearly from the handle to the spatula-shaped end.

* * * * *